United States Patent
Seto et al.

(10) Patent No.: US 6,335,075 B1
(45) Date of Patent: Jan. 1, 2002

(54) CARPET HAVING DEODORANT PROPERTIES

(75) Inventors: Yasutaro Seto, Osaka; Shuichi Gennaka, Nara, both of (JP)

(73) Assignee: Suminoe Textile Co., Ltd., Osaka (JP)

( * ) Notice: Subject to any disclaimer, the term of this patent is extended or adjusted under 35 U.S.C. 154(b) by 0 days.

(21) Appl. No.: 09/725,319

(22) Filed: Nov. 29, 2000

(30) Foreign Application Priority Data

Feb. 8, 2000 (JP) ................................. 2000-30903

(51) Int. Cl.$^7$ .............................. D03D 27/00; C11D 3/30
(52) U.S. Cl. ............................ 428/96; 510/499; 510/278; 428/82; 428/95; 428/96; 428/113; 428/357; 428/361; 428/365; 424/76.1
(58) Field of Search .................. 428/82, 95, 96, 428/113, 357, 361, 365; 424/76.1; 510/278, 499

(56) References Cited

U.S. PATENT DOCUMENTS

| | | | | |
|---|---|---|---|---|
| 5,254,386 A | * | 10/1993 | Simpson et al. | 428/95 |
| 5,690,922 A | * | 11/1997 | Mouri et al. | 424/76.1 |
| 6,077,794 A | * | 6/2000 | Tabata et al. | 442/123 |

* cited by examiner

*Primary Examiner*—Charles Boyer
(74) *Attorney, Agent, or Firm*—Wenderoth, Lind & Ponack, LLP

(57) ABSTRACT

A carpet carrying a deodorant that is resistant to washing and wear and thus capable of maintaining its deodorizing function for a long time without impairing the drape and tint of the carpet. The carpet has a backing layer and a fiber layer formed on one side of the backing layer. A deodorant is carried partially on the backing layer and partially on the fiber layer with the weight ratio of the deodorant carried on the fiber layer to the deodorant carried on the backing being 50:50 to 5:95.

5 Claims, 3 Drawing Sheets

CARPET HAVING DEODORANT PROPERTIES

BACKGROUND OF THE INVENTION

This invention relates to a carpet having a deodorizing function, i.e. which is capable of efficiently removing chemical and other malodorous substances such as formaldehyde, acetaldehyde, ammonium and acetic acid in the air.

Modern houses are highly airtight and built densely, so that various odors come from everywhere in daily life. The components causing such odors include ammonium, trimethylamine, hydrogen sulfide, methyl mercapton and acetic acid, and most notably, cigarette smoke.

Among these substances, chemical substances such as formaldehyde and acetaldehyde, which mainly originate from building materials such as floor and wall materials, reportedly cause what is now called as the "sick-house syndrome" even if their concentrations are so low as to produce no recognizable smells.

In order to remove such malodorous and chemical substances, which are odorless in low concentrations but can cause the "sick-house syndrome", from air in the house, carpets having a deodorizing function are now attracting attention.

Such conventional carpets carry a predetermined amount of deodorant on their front fibrous portion.

But the deodorant carried in such an amount that it can perform a sufficient deodorizing function tends to impair the drape or tint of the carpet and also tends to come off by friction or washing and lose its deodorizing function quickly.

An object of the invention is to provide a carpet carrying a deodorant that is resistant to washing and wear and thus capable of maintaining its deodorizing function for a long time, and is less likely to impair drape and feeling to the touch and color or tint.

SUMMARY OF THE INVENTION

According to the present invention, there is provided a carpet comprising a backing layer and a fiber layer formed on one side of said backing layer, and a deodorant carried partially on the backing layer and partially on the fiber layer.

By carrying a deodorant not only on the fiber layer but both on the fiber layer and on the backing layer, it is possible to suppress the worsening of drape and tint due to the carrying of a deodorant on the fiber layer.

By carrying a deodorant on the backing layer, too, resistances both to wear and to washing improve and good sustainability of deodorizing function can be expected. Besides, the deodorant carried on the fiber layer exhibits good initial deodorizing performance.

If the deodorant is distributed to the fiber layer and the backing layer at a weight ratio of 50:50 to 5:95, the carpet will exhibit better deodorizing function than if the total amount of deodorant is carried only to the fiber layer or only to the backing layer.

As a deodorant, an amine compound having an average particle diameter of 20 μm or under is preferable. Also, an inorganic substance may be mixed with the amine compound.

The total amount of the deodorant should be 2.5 to 30 grams per square meter and the deodorant should be distributed to the fiber layer and the backing layer at the abovesaid weight ratio.

The amine compound serves as a deodorant to remove chemical and malodor substances such as formaldehyde and acetaldehyde. The use of an inorganic substance with a deodorant makes it possible to remove chemical substances such as ammonia and acetic acid which cannot be removed by only an amine compound with a good efficiency.

Other features and objects of the present invention will become apparent from the following description made with reference to the accompanying drawings, in which:

DETAILED DESCRIPTION OF THE PREFERRED EMBODIMENT

Figure 1:
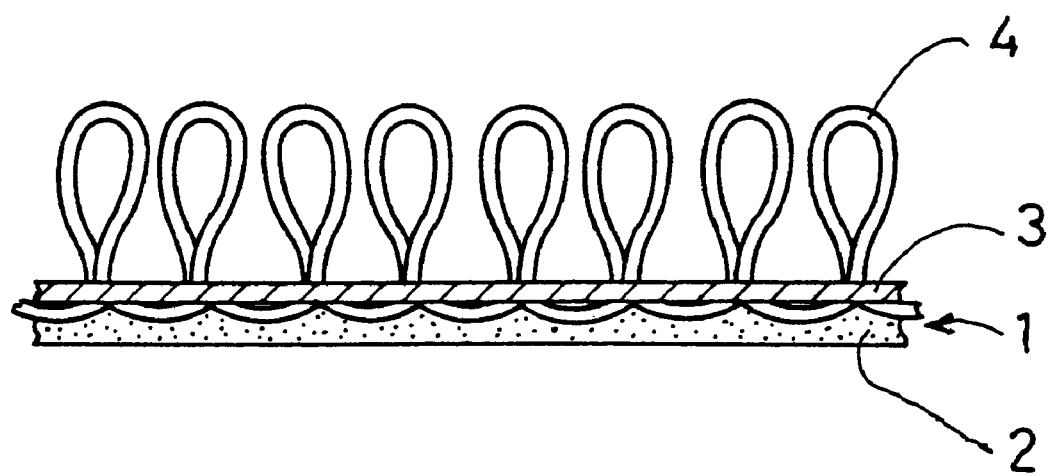
FIG. 1 is a sectional view of a carpet embodying the invention.

FIG. 1 shows a carpet embodying the present invention, which comprises a backing 2 and a fibrous layer 1 formed on the front side of the backing 2. A deodorant is carried on both the backing 2 and the front fibrous layer 1.

The front fibrous layer 1 comprises a base fabric 3 and a pile layer 4. The base fabric 3 may be a woven fabric formed by weaving yarn of a synthetic fiber such as polyester fiber, nylon fiber, polypropylene fiber or acrylic fiber, or a natural fiber such as flax, cotton or wool, a nonwoven fabric formed by mechanically joining fibers or yarns together e.g. by needling, or a nonwoven fabric formed by chemically joining fibers or yarns together e.g. with an adhesive.

The material for the pile layer 4 is not limited either, and may be a synthetic fiber such as polyester fiber, nylon fiber, polypropylene fiber, acrylic fiber or rayon fiber, or a natural fiber such as flax, cotton or wool. Also, the manner for forming the pile layer 4 is not limited. For example, it may be formed by warp or weft pile weaving like moquette, by planting pile yarn with e.g. a tufting machine, by a knitting machine, or by bonding pile yarn to the fabric 3 with an adhesive. The pile may be either cut pile or loop pile.

The material for the backing 2 is not limited either, and may be a resin composition, a rubber composition, jute, a polypropylene woven fabric or a needle-punched fabric. Among them, resin composition or rubber composition is most often used. Resins used for resin compositions usable include acrylic resins, urethane resins, polyvinyl chloride, polypropylene, ethylene-vinyl acetate copolymers (EVA). Rubbers for rubber compositions usable include SBR (styrene-butadiene rubber), MBR (methyl methacrylate-butadiene rubber), NBR (acrylonitrile-butadiene rubber), and natural rubber.

Preferable deodorants usable in this invention include amine compounds. Among them, hydrazine derivatives are especially preferable. Such amine compounds adsorb chemical substances such as formaldehyde, acetaldehyde and acetic acid. Among amine compounds, those having a low water solubility, say, 5 g/l or less at 25° C. are especially preferable, because such a compound is less likely to dissolve into water when brought into contact with water such as when the carpet is washed and maintains its deodorizing function for a prolonged period of time.

Hydrazine derivatives usable in this invention include reaction products of hydrazine compounds and long-chain aliphatic compounds or aromatic compounds.

Among them, the following reaction products are especially preferable: the reaction product of one or two compounds selected from the group consisting of hydrazines and semicarbazides and one or more kinds of compounds selected from the group consisting of monocarboxylic acids, dicarboxylic acids, aromatic monocarboxylic acids and aromatic dicarboxylic acids having 8 to 16 carbon atoms;

and the reaction products of one or two compounds selected from the group consisting of hydrazines and semicarbazides and one or more kinds of compounds selected from the group consisting of monoglycidyl derivatives and diglycidyl derivatives having 8 to 16 carbon atoms. Such hydrazine derivatives are especially high in the ability to remove odors. Specific such reaction products include, but are not limited to, dihydrazide sebacate, dihydrazide dodecanoic diacid and dihydrazide isophthalate.

Preferably, in addition to such an amine compound, an inorganic substance is used as an additional deodorant. Inorganic substances usable as the additional deodorant include, but are not limited to, activated charcoal, zeolite, monmorillonite, silica gel, and metallic oxides such as alumina, titanium oxide, zinc oxide or iron oxide. By using such additional deodorants, it is possible to effectively remove plural kinds of main harmful chemical substances that exist in the house combined with the action of amine compound.

Such an inorganic substance is preferably porous, because a porous deodorant has a large surface area and is much higher in the ability to remove harmful substances than nonporous ones. Moreover, by using a porous inorganic substance together with the amine compound, the latter compound is taken into pores of the inorganic substance, due to synergetic effect of the adsorptivity of the amine compound and the adsorptivity and decomposition property of the porous inorganic substance, their ability to remove harmful substances will be improved considerably.

There are two ways to apply the deodorant to the material to be formed into the fiber layer 1 and the material to be formed into the backing 2. One is to use a binder resin. The other is to knead the deodorant into these materials beforehand. For lower cost and higher efficiency, the former method is preferable for the fiber layer 1 and the latter method is preferable for the backing 2.

If a binder resin is used, the mixture of the binder resin and deodorant may be applied to the material by spraying, foaming, immersing, coating or padding. For higher workability and efficiency and lower cost, spraying is the best.

The binder resin may be dried in any known way such as air drying or heating, but drying by heat is preferable for higher efficiency.

For drying, it is preferably to heat at 100–180 ° C. Heating in this temperature range will allow the deodorant to stick strongly to the fibers and maintain their ability to remove harmful substances for a prolonged period of time.

The average particle diameters of the amine compound and the inorganic substance have to be 20 $\mu$m or less. If over 20 $\mu$m, they will give the carpet a rough feeling to the touch and also worsen the drape of the fiber layer 1. For better touch and drape, the average particle diameter is preferably 5 $\mu$m or under and more preferably 3 $\mu$m or under.

The binder resin used in the invention should have a glass transition point (Tg) of −30° C. or under. A binder resin having a higher Tg value will worsen the drape of the fiber layer 1. A binder resin having a Tg value of −35° C. or under is preferable.

Binder resins usable in this invention are not limited, provided they have a Tg value of −30 or under. The following are examples of such resins: self-crosslinking acrylic resin, metaacrylic resin, urethane resin, silicon resin, glyoxal resin, vinyl acetate resin, vinylidene chloride resin, butadiene resin, melamine resin, epoxy resin, acryl-silicon copolymer resin, ethylene-vinyl acetate copolymer resin, isobutylene-maleic anhydride copolymer resin, and ethylene-styrene-acrylate-methacrylate copolymer resin. They may be used singly or two or more may be mixed together as the binder resin of the invention.

If a binder resin is used, it is preferably mixed with the deodorant in the weight ratio (deodorant/binder resin) of 10/50 to 10/2. If this ratio is greater than this range, the deodorant tends to separate and thus cannot maintain their ability to remove harmful substances. If this ratio is lower than the above range, the drape of the fiber layer 1 will worsen, and also the deodorant cannot sufficiently reveal its expected function. More preferable range of the deodorant-to-binder weight ratio is 10/20–10/2.

The deodorant and the binder resin may be mixed together by dispersing them in water. In this case, the mixture has to be dispersed as uniformly as possible in water. Preferably, the binder resin is dispersed in an emulsion state with water. They may be dispersed in alcohol or other medium, but water is the most preferable. To uniformly disperse the deodorant and the binder resin in water, the deodorant alone should preferably be dispersed in water first and then the binder resin. Dispersants, thickeners or other additives may be further dispersed.

Also, anti-fungus agents, hydrophilization agents, flame retardants, or other additives may be incorporated so as not to impair the intended effects of this invention.

The total amount of the deodorant stuck on the fiber layer 1 and the backing 2 per square meter of the carpet is preferably 2.5 to 30 grams (in dry state). If the amount is smaller than this range, it cannot sufficiently reveal its expected function. Even if above this range, their ability to remove harmful substances will not improve any further but increase the cost.

The deodorant is preferably applied to the carpet such that the weight ratio of the deodorant stuck on the fiber layer 1 to that on the backing 2 is 50:50 to 5:95. It was found out by experiments that by applying the deodorant to both the fiber layer and the backing in the above ratio, its deodorizing ability improved compared with when it was applied only to the fiber layer or only to the backing as shown in FIG. 2.

Figure 2:
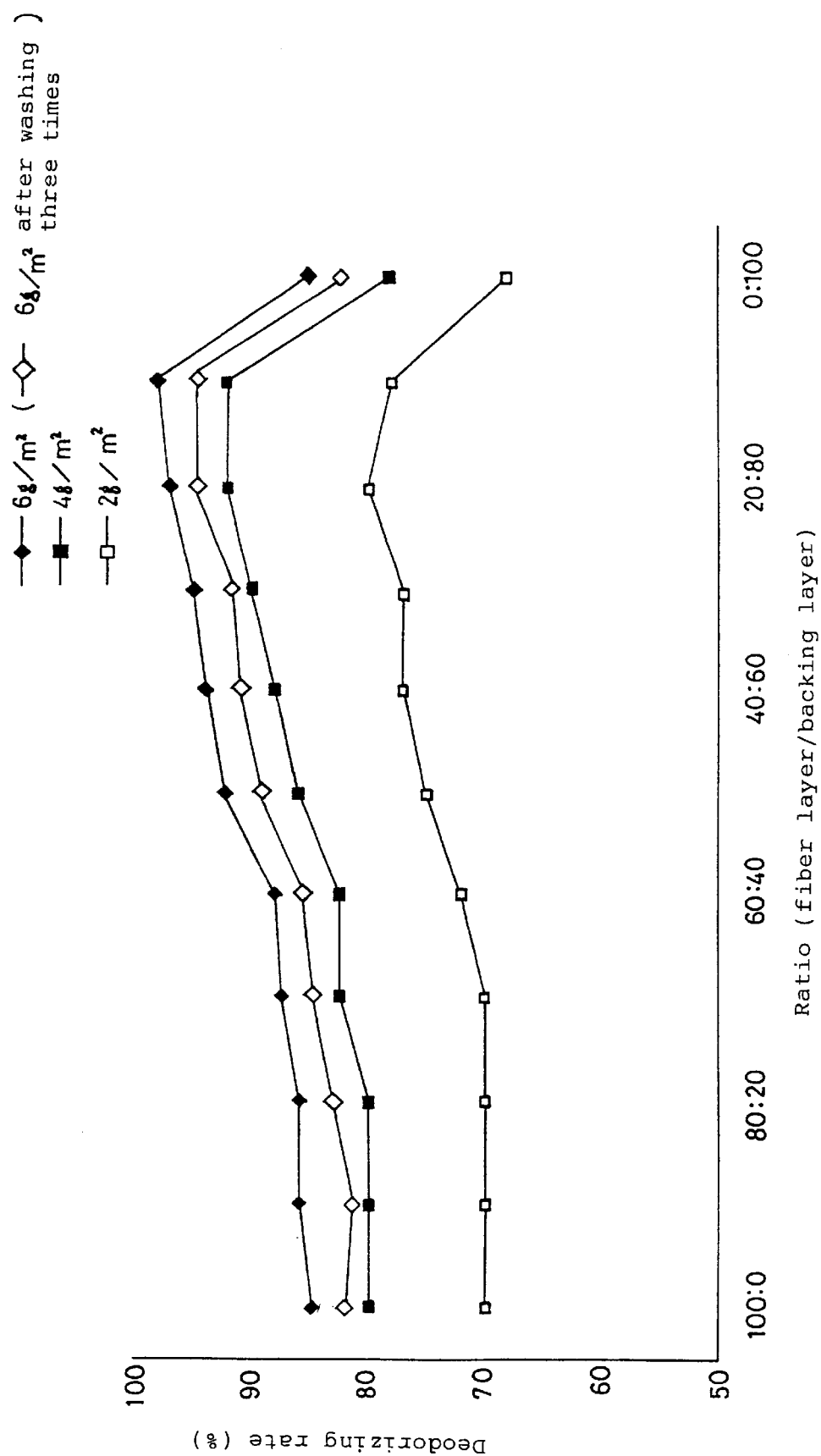
FIG. 2 is a graph showing the relationship between the deodorizing rate and the weight ratio between the deodorants carried on front and back of the carpet.

FIG. 2 shows the deodorizing rate of acetaldehyde when the deodorant was applied to the carpet in amounts of 2, 4 and 6 grams per square meter with the weight ratio of the deodorant stuck on the fiber layer 1 to that on the backing 2 adjusted to 100:0, 80:20, 60:40, 40:60, 20:80 and 0:100. As shown, deodorizing effects are far higher when the weight ratio of the deodorant was between 50:50 and 5:95 than when the deodorant was stuck only on the fiber layer or only on the backing.

Figure 3:
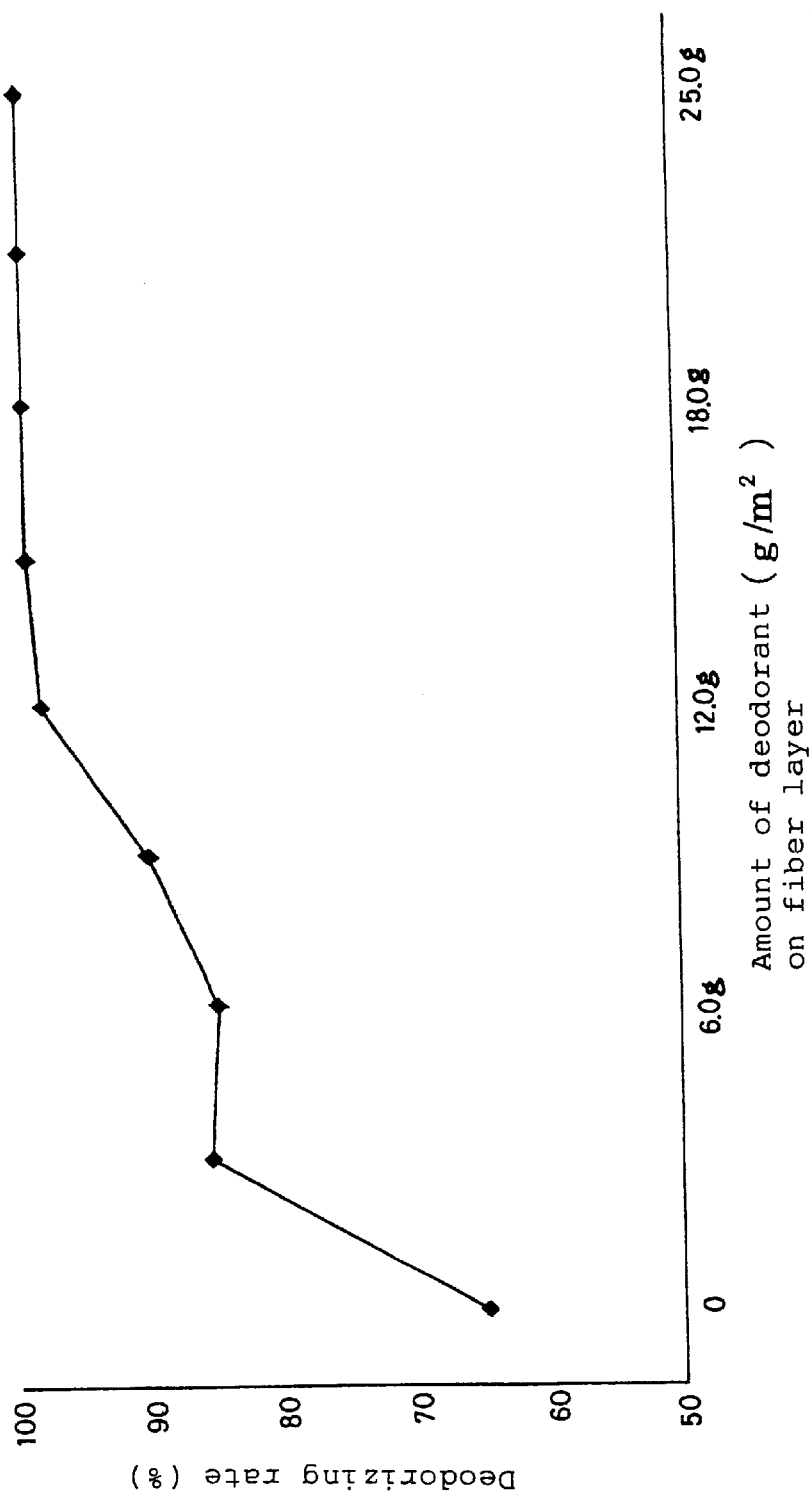
FIG. 3 is a graph showing the relationship between the deodorizing rate and the amount of deodorant applied to the carpet.

FIG. 3 shows the deodorizing rate when the deodorant was applied only to the fiber layer 1 in different amounts per square meter. As shown, when the deodorant was applied in an amount of 6 g/m$^2$, the deodorizing rate was about 85%. On the other hand, when the same amount of the deodorant was applied partially to the fiber layer 1 and partially to the backing 2 in the weight ratio between 50:50 and 5:95, the deodorizing rate was 90% or over as shown in FIG. 2 (uppermost line).

Thus, it is apparent that by applying the deodorant partially to the fiber layer and partially to the backing, it is possible to reduce the total amount of deodorant used to achieve a satisfactory deodorizing rate.

The following are materials and structure of carpet and the kind of deodorants used for the above experiments.

[Materials]

(Fiber layer)

Base fabric . . . woven fabric of polypropylene fiber

Pile layer . . . pile yarn of polyester fiber tufted to the base fabric (pile yarn weight: 700 g/m$^2$)

(Backing)

Material . . . SBR latex (Deodorant)

Material . . . dihydrazide sebacate

How the deodorant was carried: to the fiber layer (dispersion of a deodorant and a binder resin in water was stuck on the pile layer by spraying).

To the backing (deodorant dissolved and kneaded into SBR latex and the mixture applied by roller coating.

[Test and Evaluation]

(Manufacture of carpets)

[Examples in which a deodorant was applied in a total amount of 6 g/m$^2$ partially to the fiber layer and partially to the backing in a weight ratio of 20:80.]

(Backing)

A backing agent having a solid content of 70% and comprising 100 parts by weight of SBR latex (SBR content: 50 wt %) and 400 parts by weight of calcium carbonate with 5 parts by weight of dihydrazide sebatate (average particle diameter: 4 $\mu$m) dispersed and kneaded thereto was applied to the backing by roller coating at a rate of 700 g/m$^2$ (in wet state) and dried at 150° C. to form the backing.

(Front fiber layer)

A dispersion was formed by adding 2.4 parts by weight of dihydrazide sebacate having an average particle diameter of 4 $\mu$m to 92 parts by weight of water and agitating the mixture with a stirrer. 2.4 parts by weight of an acrylic rein (binder resin; −37° C. Tg) was added to the dispersion and the mixture was well agitated to form a uniform dispersion. The dispersion was applied to the fiber layer of the carpet (with the backing layer already formed) by spraying at the rate of 50 g per square meter, and the carpet was dried at 130° C. for ten minutes.

[Other Examples]

(Backing)

A backing agent having dihydrazide sebacate (average particle diameter: 4 g m) dissolved and kneaded was applied to the backing of each carpet specimen in amounts shown in FIG. 2.

(Front fiber layer)

A dispersion of acrylic resin as a binder resin (Tg: −37° C.) in water was formed so that the amount of dihydrazide sebacate (average particle diameter: 4 $\mu$m) will be as shown in FIG. 2. The dispersion was applied to the fiber layer of each carpet specimen by spraying at the rate of 50 grams per square meter and dried at 130° C. for ten minutes to manufacture carpets.

(Ability to remove acetaldehyde)

A test piece (10×10 cm square) cut out of each carpet specimen was put in a bag having a capacity of 3L, and acetaldehyde gas was injected into the bag to a concentration of 200 ppm. After 48 hours, the concentration of acetaldehyde gas in the bag was measured, and based on the measured value, the total amount of acetaldehyde gas that has been adsorbed and removed by the test piece of the carpet was calculated to obtain a removal rate (%) of acetaldehyde gas.

(Removing function sustaining test)

Each carpet specimen was subjected to removing function tests in the manner mentioned above before and after it was washed three times and dried, and the removing function sustaining rate (%) was calculated as follows:

Sustaining rate (%)=(adsorption amount after washing) ÷(adsorption amount before washing)×100

(Drape test)

Each carpet was touched by hand to evaluate drape (or hardness). The carpets carrying a deodorant both on the front fiber layer 1 and the backing 2 was smooth to the touch and good in drape too.

What is claimed is:

1. A carpet having a deodorizing function, said carpet comprising a fiber layer having base fabric and a pile layer provided on said base fabric so as to protrude from one side of said base fabric, said fiber layer carrying a first deodorant, and a backing layer formed on the other side of said base fabric and made of a rubber or resin conposition, said backing layer having a second deodorant kneaded therein, said first and second deodorants both containing an amine compound having an average particle diameter of 20 $\mu$m or under, the weight ratio of said first deodorant to said second deodorant being 50:50 to 5:95, the total amount of said first and second deodorants applied to the carpet being 2,5 to 30 grams per square meter.

2. The carpet as claimed in claim 1 wherein said first and second deodorants contain an amine compound having an average particle diameter of 20 $\mu$m or under and an inorganic substance.

3. The carpet as claimed in claim 1 wherein said first deodorant is applied by spraying or foaming.

4. The carpet as claimed in claim 1 wherein the weight ratio of said first deodorant to said second deodorant is 20:80 to 10:90.

5. The carpet as claimed in claim 1 wherein the weight ratio of said first deodorant to said second deodorant is 10:90.

* * * * *